(12) United States Patent
Everett (10) Patent No.: US 7,326,385 B2
(45) Date of Patent: Feb. 5, 2008

(54) PLATE AND METHOD FOR HIGH THROUGHPUT SCREENING

(75) Inventor: Keith Everett, Raleigh, NC (US)

(73) Assignee: Biolex Therapeutics, Inc., Pittsboro, NC (US)

( * ) Notice: Subject to any disclaimer, the term of this patent is extended or adjusted under 35 U.S.C. 154(b) by 901 days.

(21) Appl. No.: 10/157,562

(22) Filed: May 29, 2002

(65) Prior Publication Data

US 2003/0026738 A1    Feb. 6, 2003

Related U.S. Application Data

(60) Provisional application No. 60/294,430, filed on May 30, 2001.

(51) Int. Cl.
*B01L 3/00* (2006.01)

(52) U.S. Cl. ..................... 422/102; 422/104

(58) Field of Classification Search .......... 422/102; 117/206
See application file for complete search history.

(56) References Cited

U.S. PATENT DOCUMENTS

| | | |
|---|---|---|
| 2,533,089 A | 12/1950 | Brewer et al. |
| 4,125,436 A | 11/1978 | Liner |
| 4,531,324 A | 7/1985 | Yang et al. |
| 4,812,392 A | 3/1989 | Miyake et al. |
| 4,871,674 A | 10/1989 | Matsui et al. |
| 4,917,793 A | 4/1990 | Pitt et al. |
| 4,963,490 A | 10/1990 | Churchouse et al. |
| 4,980,293 A * | 12/1990 | Jeffs .................... 436/180 |
| 5,026,649 A | 6/1991 | Lyman et al. |
| 5,141,718 A | 8/1992 | Clark |
| 5,212,906 A | 5/1993 | Okuno et al. |
| 5,215,920 A | 6/1993 | Lyman et al. |
| 5,262,128 A | 11/1993 | Leighton et al. |
| 5,324,657 A | 6/1994 | Tanny |

(Continued)

FOREIGN PATENT DOCUMENTS

EP    0 483 620 A    5/1992

(Continued)

OTHER PUBLICATIONS

Small Parts Inc., Porous Plastics, pp. 2-3.

(Continued)

*Primary Examiner*—Jill Warden
*Assistant Examiner*—Natalia Levkovich
(74) *Attorney, Agent, or Firm*—Alston & Bird LLP (57) ABSTRACT

A multiple well plate and method for media exchange, including a body defining a plurality of cell wells each connected via a channel to one of a plurality of aspiration holes, is provided. The cell wells contain a porous, hydrophilic frit which is suspended on a ledge above a reservoir of fluid media and supports a tissue sample. The properties of the frit wick the fluid media upwards to supply the tissue sample with nutrients for growth and proliferation. Old media is aspirated from the wells by a liquid handling device which inserts a pipette tip into the aspiration holes. The pipette tip applies a suction pressure which draws the media out of the cell well, through the channel, into the aspiration hole and out through the pipette tip. New media is dispersed through the pipette tip and directly into the cell well.

15 Claims, 6 Drawing Sheets

U.S. PATENT DOCUMENTS

| | | | |
|---|---|---|---|
| 5,358,871 A | 10/1994 | Stevens et al. | |
| 5,376,273 A | 12/1994 | Pacheco et al. | |
| 5,466,602 A | 11/1995 | Lyman et al. | |
| 5,468,638 A | 11/1995 | Barker et al. | |
| 5,525,505 A | 6/1996 | Young et al. | |
| 5,597,731 A | 1/1997 | Young et al. | |
| 5,641,681 A * | 6/1997 | Carter | 436/4 |
| 5,650,323 A | 7/1997 | Root | |
| 5,707,869 A | 1/1998 | Wolf et al. | |
| 5,801,055 A | 9/1998 | Henderson | |
| 5,817,510 A | 10/1998 | Pandey et al. | |
| 5,958,762 A | 9/1999 | Stoppini et al. | |
| 5,972,694 A | 10/1999 | Mathus | |
| 6,037,171 A | 3/2000 | Larsson | |
| 6,146,883 A | 11/2000 | Grass | |
| 6,306,645 B1 | 10/2001 | Tanklevsky et al. | |
| 2001/0002984 A1 * | 6/2001 | Vetter | 422/102 |
| 2002/0172621 A1 * | 11/2002 | Barbera-Guillem | 422/100 |

FOREIGN PATENT DOCUMENTS

| | | |
|---|---|---|
| EP | 0 590 485 A | 4/1994 |
| EP | 0 590 513 A | 4/1994 |
| WO | WO-91/05519 | 5/1991 |
| WO | WO 99 55827 A | 11/1999 |
| WO | WO 00 72968 A | 12/2000 |

OTHER PUBLICATIONS

Tecan, Temperature Controlled Deck.
Tomtec, Quadra 96 Plus—A Multi-Purpose Microplate Workstation.
Genetix, Qbot Details (visited Jan. 14, 2000) http://www.genetix.co.uk/Qbotdt.htm.
Millipore Catalog, MultiScreen Vacuum Manifold Materials (visited May 3, 2001) http://www.millipore.com/catalogue.nsf/docs/C6639.

* cited by examiner

PLATE AND METHOD FOR HIGH THROUGHPUT SCREENING

CROSS-REFERENCE TO RELATED APPLICATIONS

The present application claims priority from U.S. Provisional Application No. 60/294,430 entitled "Plate and Method for High Throughput Screening" filed on May 30, 2001, the contents of which are incorporated herein by reference.

FIELD OF THE INVENTION

The present invention relates to devices and methods for promoting the growth of tissue in experimental and production settings, more particularly the use of specialized plates to house the tissue and the cycling of media to biologically sustain the tissue.

BACKGROUND OF THE INVENTION

High-throughput screening typically requires parallel processing of batches of samples, typically in multiple well plates (MWPs) of 24, 48, 96, and 384, or more, wells per plate. MWPs are standard sizes that can be used with existing high-throughput machinery, such as with robotic-controlled pipetters. Each pipetting station of a robotic controlled pipetter employs pipetting heads having an array of pipette tips that address multiple wells simultaneously. Although used effectively for the screening of liquid samples, the current multiple well plates are generally ineffective for screening plant and other tissues, and the secretory products associated with these tissues, that require, or prefer, more complex environments such as solid support structures.

For example, attempts have been made to grow plants in MWPs by suspending the plants in a liquid media within each well. However, the plant tissue is deprived of oxygen when sitting in the liquid, effectively "drowning" the plant tissue in an anaerobic environment. Other attempts have been made using media that are generally more solid and provide a substrate on which the plant tissue may be supported above the fluid, such as a gel or filter paper disk. Although these types of supports avoid drowning the plants, they are difficult to exchange and replenish when the nutrients or media have been depleted. Paper bridges doused in liquid media have also been used as tissue supports and the liquid media is somewhat more easily replenished. However, empirical evidence has shown that paper bridges are difficult to manage in an automated system and are generally ineffective at promoting plant tissue growth. Without being wed to any particular theory, this may be because the liquid media does not easily penetrate the paper bridge (i.e., the paper bridge is only mildly hydrophilic) and the tissue supported thereon lacks a continuous supply of media.

A common approach to supplying fresh media to plant tissue is to move the plant tissue to a container holding fresh media. Movement of the plant tissue is a relatively slow and labor intensive process, as multiple plates must be replenished and otherwise prepared for each batch of plant tissue. In addition there is a threat of loss or contamination of the tissue samples when they are removed from the wells.

Another approach to aspirating and removing spent media and tissue byproducts is to use an assay plate having a plurality of wells, with each well having a hole or port at the base of the well. A filter is positioned at the bottom of each well to support the tissue. Spent media can be vacuum harvested from each well through the port using a vacuum manifold assembly. One example of a vacuum manifold assembly is the MultiScreen Vacuum Manifold system manufactured by MILLIPORE of Bedford, Mass. The assay plate rests on a manifold that supplies a vacuum which draws the media through the filter disks, out of the cell wells and through the ports, where it is captured in the manifold below. Although the filter disks in the assay plate allow media to be drawn out of the plate, it is difficult for the filter disks to retain enough media to support tissue maintenance and growth for any length of time. Because the ports at the bottom of the wells are open to the ambient air, the ports may allow media to leak or evaporate and may also provide a path for microbial contamination of the wells. In addition, the wells of the assay plate cannot be individually sampled because the vacuum manifold harvests the media from all of the wells at once.

The tissue of animals, and other types of organisms may also require, or prefer, solid support structures that inhibit the use of multiple well plates and high-throughput screening techniques. For instance, the growth of cartilage cells may be promoted by the use of a collagen fibril matrix that simulates an in vivo environment. Similar to the plant tissue discussed above, the cartilage cells need a supply of fresh media that is replenished at various intervals to survive and/or proliferate. In addition, some of the cartilage cells proliferate within the collagen fibril matrix and cannot be moved independent of the matrix. Moving the cells to a new plate with a fresh supply of media requires movement of the entire collagen matrix which is a relatively slow and inefficient process that exposes the tissue to contamination.

It would be advantageous to have a multiple well plate that allows the use of high throughput screening methods for non-liquid samples. In addition, it would be advantageous to have a multiple well plate that allows the use of high throughput screening methods for tissues that require, or prefer, solid support structures. It would be further advantageous to have a multiple well plate that promotes the growth of tissue, such as plant tissue, without posing the risk of drowning the tissue in liquid media or allowing the tissue to dehydrate or become contaminated. It would also be advantageous to have a multiple well plate that allows media to be easily replenished, without undue disturbance of the tissue contained in the wells. Additionally, it would be advantageous to have the capability of sampling less than the total number of wells in the plate without disturbing the unsampled wells.

SUMMARY OF THE INVENTION

The present invention addresses the above needs and achieves other advantages by providing a multiple well plate (MWP) and method for media exchange that promotes the growth of plant tissue, and other types of tissue, by controlling the supply of media to the tissue and allowing for the regular exchange (removal and addition) of media without disturbing the tissue. The MWP includes an array of wells, with each well being coupled with an adjacent aspiration hole that allows media to be aspirated from the wells using a conventional, automated pipette head. The MWP and pipette head provide a virtually complete exchange of the spent media because of the novel dual-well architecture. A hydrophilic, porous frit housed within each well supports the tissue and holds the media in its interstices, allowing contact between the tissue and the media while avoiding an anaerobic condition. The media is wicked upwards in sufficient quantities to provide nutrients to the tissue and promote proliferation of the tissue.

In one embodiment, the invention includes a plate for holding a porous frit that supports a tissue. The porous frit is saturated in a media that may be regularly aspirated and refreshed, for example, by a top-loading pipette device. The plate comprises a body with an upper surface defining a first hole and a second hole. The first hole has a first hole upper edge defined by the upper surface of the body and a first hole bottom portion defined within the body and below the upper surface of the body. The first hole is configured to receive the porous frit and the tissue, and to hold the media bathing the porous frit and the tissue. The second hole has a second hole upper edge defined by the upper surface of the body and a second hole bottom portion defined within the body and below the upper surface of the body. The second hole bottom portion is in fluid communication with the first hole bottom portion so that the pipette device can access the second hole upper edge to aspirate the media by applying a vacuum. The pipette device also refreshes the media by adding fresh media directly onto the frit in each well.

In another aspect, the body of the plate further defines a passage connecting the first hole bottom portion and the second hole bottom portion in fluid communication. The body may further include a ledge protruding into the first hole bottom portion for supporting the frit above a reservoir of fluid. The body may also define a plurality of the first and second holes, with each first hole in fluid communication with a respective one of the second holes to form a MWP. In another aspect, the body defines an array of first and second holes, for example 12, 24, 48, 96, 384, or 1536 first and second holes, wherein each first hole is in fluid communication with a respective one of the second holes. The first and second holes preferably have cylindrical shapes.

In yet another aspect, the top surface of the body is configured to receive a cover plate disposed thereon. Preferably the cover plate is transparent to light transmission and the first hole upper edge is configured to also allow light transmission, thereby promoting plant tissue growth.

In another embodiment, the present invention includes a method of making a plate for holding a porous frit that supports a tissue wherein the porous frit is saturated in a media. The media is regularly aspirated and refreshed by a pipette device to promote proliferation of the tissue. The method includes providing a body with an upper surface and defining a first and second holes in the body. Defining a first hole in the body includes drilling through the upper surface of the body to form a first hole upper edge and drilling below the upper surface to form a first hole bottom portion. The second hole is defined by drilling through the upper surface of the body to form a second hole upper edge and drilling below the upper surface to form a second hole bottom portion. The first and second hole bottom portions are connected in fluid communication by forming a passage in the body and between the first hole bottom portion and the second hole bottom portion. Preferably, the passage is formed by inserting a saw disc into the first hole bottom portion and moving the saw laterally until encountering the second hole bottom portion.

In yet another embodiment, the present invention includes a method of using a MWP. A frit is placed into each of the plurality of first holes and tissue, preferably a duckweed or other plant tissue, is placed onto the frit. A media is dispensed into each of the plurality of first holes. A pipette is inserted into each of the plurality of second holes and used to aspirate the media from the first holes. The media is aspirated by applying a suction pressure to the second holes using the pipette. The suction pressure draws the media from the first hole, into the second hole and into the pipette so as to flush the media from the plate. Fresh media can be re-dispensed into the plurality of first holes after aspirating the media from the second holes.

In still another embodiment, the present invention includes a frit material for supporting a tissue having a porous structure, a top surface and a bottom surface. The porous structure has hydrophilic properties and a plurality of interstices. The top surface is configured to support the tissue. The bottom surface is in fluid communication with a reservoir of fluid media. The hydrophilic properties of the porous structure wick the fluid into its interstices so that the supported tissue is supplied with sufficient liquid media from the reservoir to promote growth of the tissue.

The present invention has several advantages. For example, the tissue samples in the wells do not have to be moved or disturbed when the provided media is spent, cutting down on workload and ensuring sterile and optimal growth conditions. The plates may be used with conventional liquid handling pipette heads of the fixed tip or individually controllable tip versions because the aspiration holes are accessible from the upper surface of the body, i.e., a top-loading arrangement. The use of robotic liquid handlers with the plate promotes a well-to-well consistency in the treatment of the tissue, as well as the efficient removal and replacement of the media. The top-loading aspect allows the use of a standard lid for sterility control and removes the need for a separate vacuum manifold station for pulling out media. The lack of a manifold allows for the differential treatment of each well and provides flexibility in liquid handler design and selection, as well as experimental model and sample interrogation functions. The liquid head can be configured to remove the media as well as add new media with no change of tooling or pipette tips.

BRIEF DESCRIPTION OF THE DRAWINGS

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
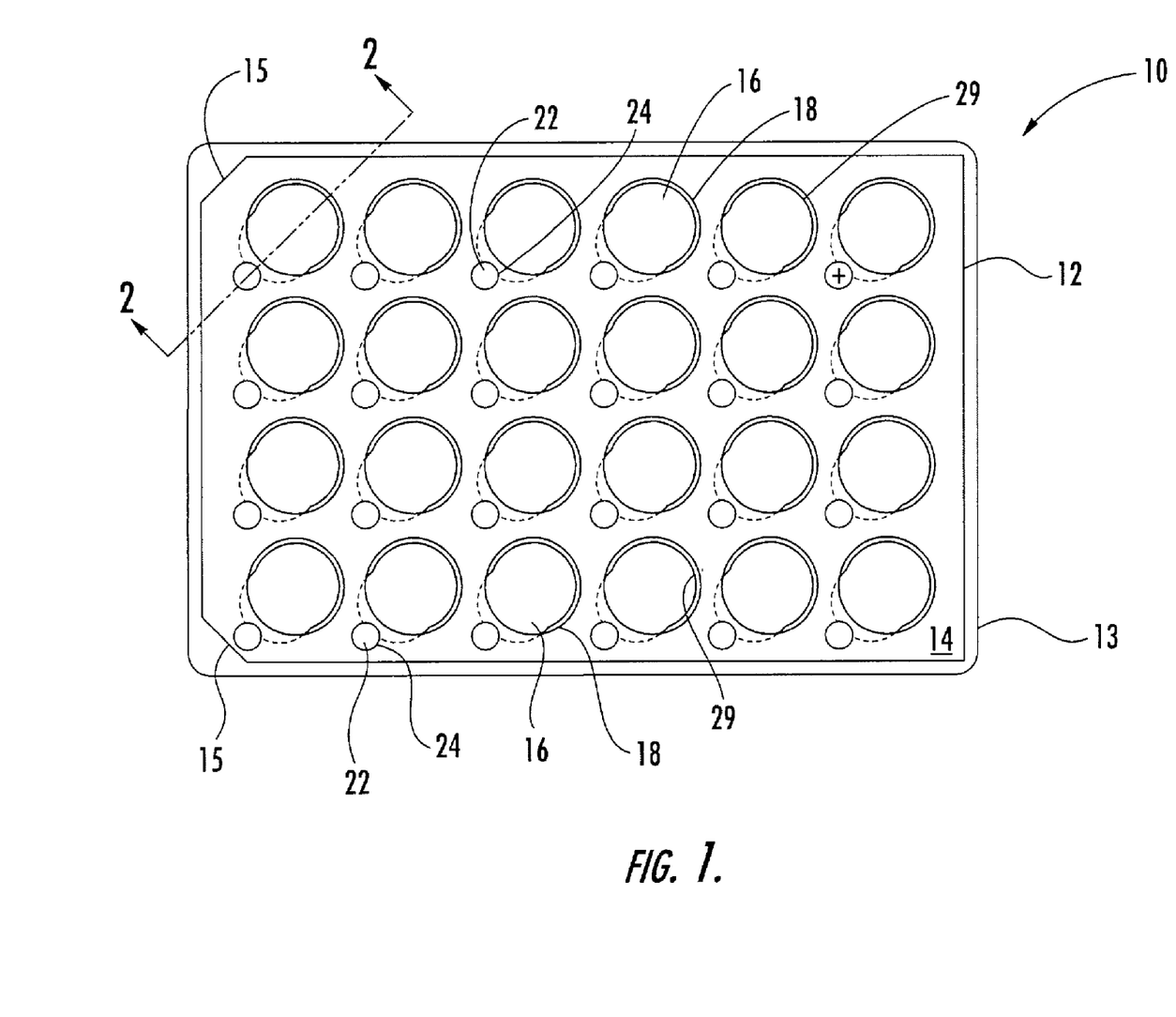
FIG. 1 is a plan view of a MWP for liquid media exchange of a first embodiment of the present invention.
Figure 2:
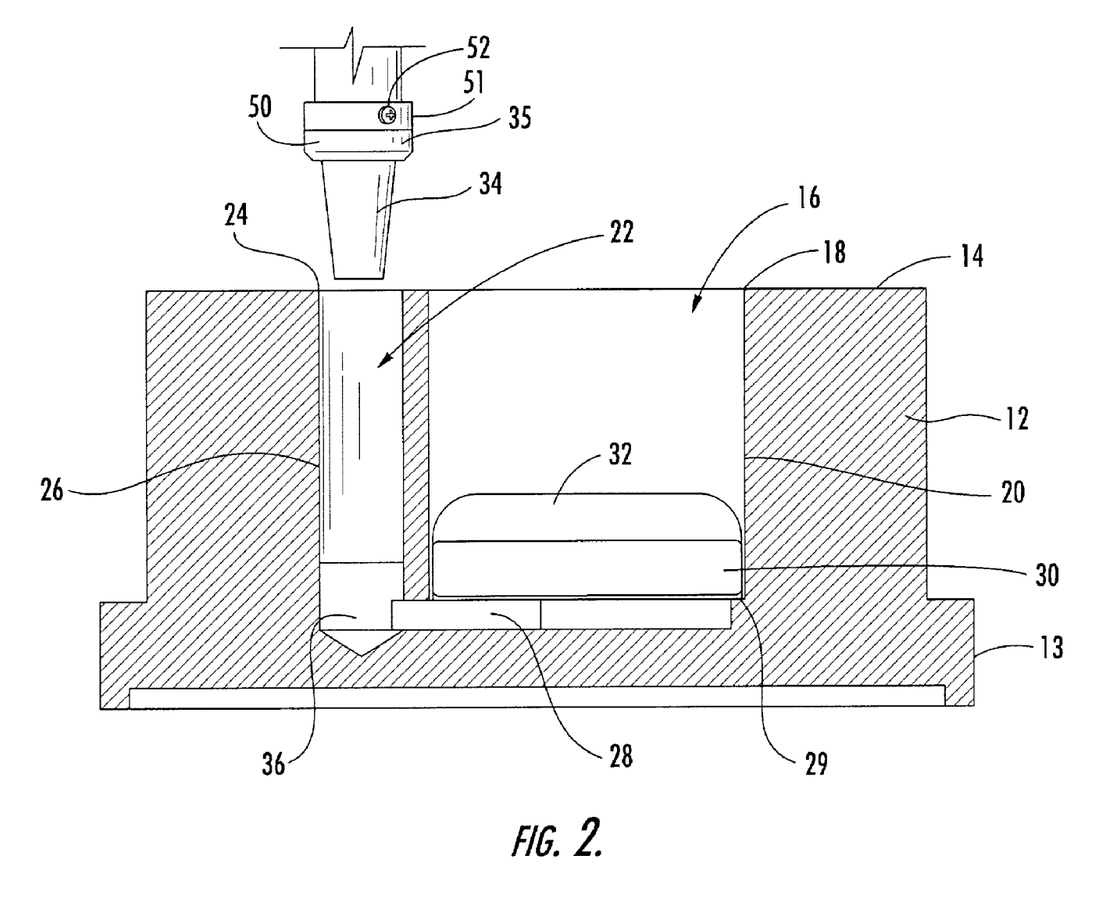
FIG. 2 is an enlarged, cross-sectional view of a single well and an aspiration hole from the MWP of FIG. 1.

A multiple well plate (MWP) 10 of the present invention includes a body 12 having an upper surface 14. The body 12 defines an array of first holes, or wells 16 and an array of second aspiration holes 22, as shown in FIG. 1. A plurality of channels 28 each connect a respective one of the wells 16 to an adjacent one of the aspiration holes 22, as shown in FIG. 2. In one embodiment, disposed in each of the wells 16 is a porous, hydrophilic frit 30 which supports a tissue sample 32 over a reservoir of liquid media 36. The porous, hydrophilic properties of the frit 30 wick the media 36 upwards, so as to supply the media to the tissue sample 32. Exchange of old, depleted media 36 is facilitated by the aspiration holes 22 which are each sized and configured to receive a pipette tip 34. During aspiration, several of the pipette tips are inserted into the aspiration holes 22 and apply a vacuum pressure. The vacuum pressure draws the fluid media 36 out of each of the wells 16, through the channels 28, through the adjacent one of the aspiration holes 22 and into the pipette tips.

The tissue sample 32 is preferably a plant tissue, such as dicot and monocot tissue such as tissue from corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza saliva*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers. In some embodiments the tissue is callus tissue from duckweed or gymnosperms. The present invention may be particularly effective with plant tissues that thrive with minimal fluid, such as tissue derived from gymnosperms.

The body 12 of the MWP 10 is preferably constructed of a polycarbonate block that can be machined and is resistant enough to heat to be sterilized in an autoclave for reuse. Generally, the hardness of polycarbonate allows it to be machined by computer controlled milling machine (CNC), or other automatic machining process, into complex, precision shapes. The body could also be constructed of other materials, such as a polystyrene, polysulphone, other synthetic materials, metals, ceramics, glass, etc. The body 12 is rectangular in shape, being 5.03±0.01 inches in length, 3.365±0.01 inches in width and 0.813±0.01 inches in height, a configuration compatible with most conventional liquid handling machines. The body 12 includes other features such as a base 13 and a pair of 45° chamfers 15 on opposing corners of one width of the body. The base 13 provides a ledge and can serve as a gripping or mounting surface in conventional equipment. The pair chamfers 15 can serve as reference marks to ensure the proper orientation of the body, especially when it is important to keep track of the location of each well. The body 12 also has a flat, upper surface 14 through which the holes 16 and 22 are drilled. It should be noted, that although the size of the body is preferably configured for compatibility with preexisting equipment, the dimensions of the body can be varied as desired.

The number, dimensions and locations of the wells 16 are also tailored to be compatible with preexisting equipment. For instance, the plate preferably has 24 wells in an array of 4 by 6, or 48 wells in an array of 6 by 8 to be compatible with most liquid handling devices. Other well densities could be used such as 6 wells, or 96 wells that are compatible with conventional devices. However, nonstandard well densities could also be used, such as single well or a 1000 wells. Generally the number of wells will be limited by such practicalities as the size of the body 12, the type of tissue being grown, the capabilities of the equipment using the wells and the size of the wells themselves.

Preferably, each of the wells 16 has a standard cylindrical shape with a diameter of 0.62 inches and a depth of 0.60±0.01 inches for the 24 well plate. The diameter of each well can be varied as desired, and is based on several factors, such as the initial size of the tissue to be placed in the well, the growth rate of the tissue, and the length of time the tissue is to be propagated in the well before removal. A center-to-center distance between the wells is 0.76 inches for the 24 well plate to ensure that the arrangement and motion of standard, automated pipette devices is compatible. The 24 well plate has been determined by the inventors to be particularly suitable to the tissue propagation of duckweed callus, presenting a preferred balance of tissue 32 volume and density of wells. The density of the cell wells 16 used for duckweed is preferably 96 wells or less due to the size of callus and rapid cell growth. Of course, other arrangements could also be used for more customized equipment, if desired.

The aspiration holes 22 extend through the upper surface 14 of the body 12. Each of the 24 aspiration holes 22 is preferably adjacent to, and connected in fluid communication with, a respective one of the wells 16. The pairing arrangement of the aspiration holes 22 and the wells 16 allows aspiration without cross-contamination of the samples, such as occurs with the prior art manifold well plates. In addition, the pairing arrangement allows the media of individual wells 16 of interest to be aspirated and refreshed selectively. Individual wells 16 could be addressed selectively by hand or by automated equipment that allows the operation of a single pipette independently of the other pipettes in the head. Selectively addressing wells would be useful if, for instance, the tissue in one of the wells was generating a strong expression response to an agent, such as increased growth of tissue, increased expression of a polypeptide, added resistance to a selective agent such as a herbicide, or resistance to a plant pathogen. Other biochemical or biophysical responses could also be assayed in individual wells with the present invention. The media from this well could be aspirated and tested more frequently than the other wells. Among other advantages, more frequent collection and testing of media from that well would provide a stronger statistical correlation. If contamination is less of a concern, each of the aspiration holes 22 could be paired with several wells 16 to cut down on the number of aspiration iterations.

Each of the aspiration holes 22 are also preferably cylindrical in shape with a depth of 0.66±0.01 inches and a diameter of 0.167 inches, so as to be able to receive a standard sized pipette tip 34 through its upper edge 24. Larger or smaller diameters, and different center-to-center distances could be used, depending upon the size of the pipette tip to be inserted therein. Of course, the other shapes and other dimensions could be varied to suit a customized arrangement, or other standard pipette shapes and lengths that are known to those of skill in the art. Cylindrical aspiration holes 22 are also preferable in that they are easier to machine with rotating drill bits. The center-to-center distance between adjacent ones of the aspiration holes 22 is preferably the same as the center-to-center distance between the wells 16, which is 0.76 inches in the illustrated embodiment of 24 wells. The placement of the aspiration holes through the upper surface 14 of the body 12 and the same center-to-center distance ensures that the same pipette head configuration can be used for aspiration of the media 36 as for the dispersion of the media.

Each of the channels 28 connects a respective pair of the cell wells 16 and aspiration holes 22 in fluid communication, as shown in FIG. 2. Each of the channels 28 is preferably roughly elliptical in shape due to the preferred method of manufacturing used to create the channel, as will be described hereinafter. Each of the channels is disposed beneath a bottom portion of one of the wells 16 and the aspiration holes 22, also due to the preferred method of manufacture. Many types of shapes could be used for the channel 28 as the pressure distribution of the vacuum applied by the pipette 34 will still be evenly distributed throughout the cell well being aspirated. Each of the channels 28 acts, along with its respective one of the wells 16 and the holes 22, as a reservoir for excess media 36 that has not been wicked into the frit 30. In addition to supplying a vacuum for aspiration, the channels 28 and aspiration holes 22 could also be used to supply media 36. Supplying media through the channels 28 and aspiration holes 22 to the wells 16 could be useful, for instance, if the callus of the plant tissue 32 was dense enough to be relatively impermeable to media dispensed into through the upper edge of the wells 16. Preferably, the width of each of the channels 28 is less than the diameter of its respective one of the wells 16 so as to form a ledge 29 at the bottom of the well for supporting the frit 30 above the media 36.

Each frit 30 is preferably constructed of a sintered polyethylene material that is porous and hydrophilic to promote the attraction and retention of the media within its interstices. The hydrophilicity of the frit material can be permanent or temporary depending upon the processes by which it is applied, or whether the material is inherently hydrophilic. Alternative materials with porous structures could be used and a surfactant could be applied to materials not naturally hydrophilic to make them hydrophilic. The material is produced by sintering and wicks solutions by capillary action and can act as a sterile barrier due to its tortuous path properties. The frits are preferably cut or punched in disk shapes roughly congruent with the wells 16 from porous ¼ inch thick polyethylene sheet with an average pore size of 90 to 130 micrometers known as Porex from Porous Products of Fairburn, Ga. and also available as Part No. Y2-PEH-250/90 from Small Parts Inc., Miami Lakes, Fla. Such a frit can hold about 550 µl of media and supply the tissue for a number of days.

The congruency of shape between the frit 30 and its respective one of the wells 16 ensures a fit with minimal leakage of the media 36 around the frit and also ensures that the frit rests firmly on the ledge 29, above most of the media. Different thicknesses of the frit 30 may be used, with thicker frits generally holding more material and needing to be refreshed with new media less often. A larger diameter frit could be used for larger diameter wells 16, but may require a manifold underneath for additional support to keep the large diameter frit 30 from collapsing under the applied vacuum pressure. For instance, a large diameter frit 30 could be supported by a screen disposed on the back of the frit material when the frit material is manufactured. Despite the possible need for a supporting manifold, the frits are typically much stronger than similarly sized membranous or paper supports which cannot withstand even moderate vacuum pressures applied by the pipette tip during aspiration. Preferably, the frit material of the present invention should be able to withstand pressures of about 30 inches of Hg. In yet another embodiment, the tissue 32 could be grown on a sheet of the frit material, and then cut or punched into individual frits for placement into the wells 16.

Figure 6:
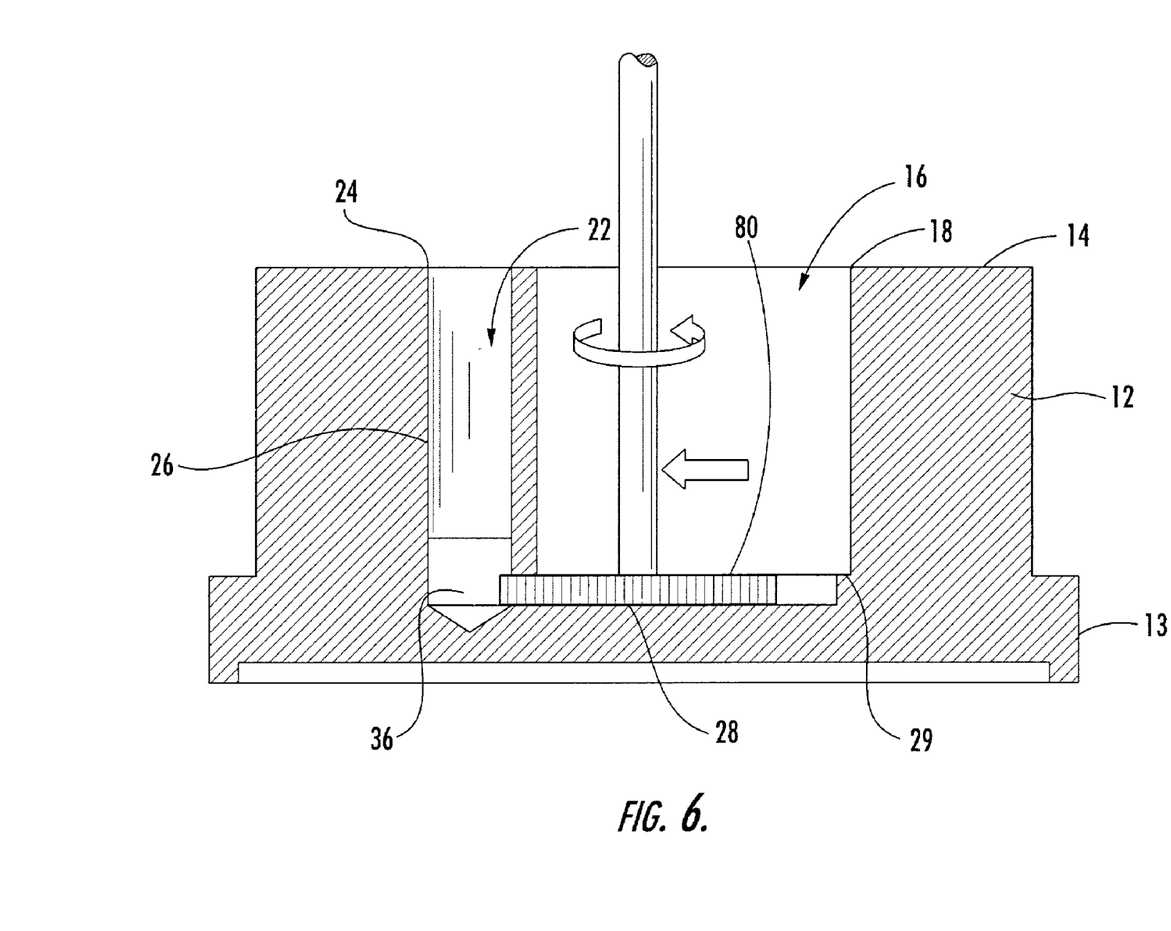
FIG. 6 is a sectional view of the well and aspiration hole of FIG. 2 being machined in another embodiment of the present invention.

The MWP 10 is preferably constructed from a block of polycarbonate material of roughly the same rectangular dimensions as the body 12. Constructing the plate from a single block of material insures against leakage between wells which could result in cross-contamination of the samples. The wells 16 and aspiration holes 22 are preferably formed using a CNC, or other automated drilling machine, with drill bits of similar dimensions to the desired hole dimensions. If necessary, the drilling machine also cuts away enough polycarbonate to form the base 13, the inset above the base, the chamfers 15 and removes enough material to flatten out other surfaces, such as the upper surface 14. The channel 28 is preferably formed using a rotating saw blade 80 on the same milling machine. The rotating saw blade has a cutting diameter of slightly less than the wells 16 and is inserted into one of the wells until it cuts away to a depth equal to the thickness of the rotating saw blade 80, as shown in FIG. 6. The rotating saw blade is then advanced in the direction of the adjacent one of the aspiration holes 22 until it cuts into the aspiration hole enough to form the channel 28 with sufficient size to enable fluid communication between the well and the aspiration hole, as shown in FIG. 2. The saw blade 80 is then moved back to the center of the well and retracted out of the well. The undersized diameter of the saw blade forms the ledge 29 on which the frit 30 is supported.

Figure 3:
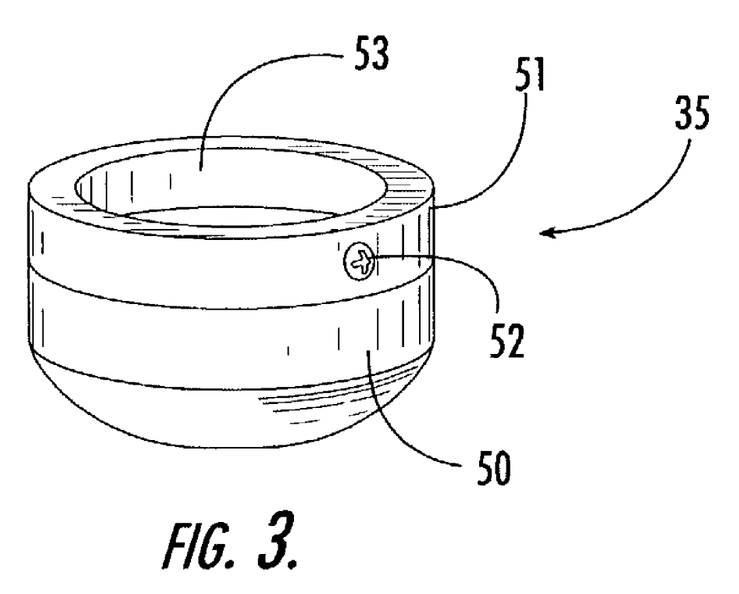
FIG. 3 is a perspective view of a tip seal of another embodiment of the present invention.

As shown in FIGS. 2 and 3, the present invention can also include a seal 35 that embraces the pipette tip 34 and is disposed around the upper edge 24 of one of the aspiration holes 22 when the tip is inserted therein. The seal 35 includes an elastomeric ring 50 subjacent a rigid collar 51. The rigid collar is preferably constructed from a stiff material, such as from a steel bushing, and optionally includes a set screw 52 extending through its side. Tightening of the set screw tightens the collar about the pipette tip 34 allowing the rigid collar 51 to prevent upward migration of the elastomeric ring 50 as it is pressed against the upper edge 24 of the aspiration hole. The end of the elastomeric ring 50 that makes contact with the upper edge 24 of the aspiration hole can have a frustoconical shape with a preferred angle of about 70° to further facilitate formation of a vacuum-tight seal. Further preferably, the seal 35 is approximately 0.3 inches in diameter and 0.5 inches long so as to fit a standard pipette tip. For instance, TECAN pipette tip No. 71-700S with a PTFE (TEFLON) coating, an inside point diameter of 0.5 mm, outside point diameter of 1.1 mm, inside body diameter of 1.5 mm and an outside body diameter of 2.0 mm.

The elastomeric ring 50 may also be configured to fit any type of pipette tip by sizing its aperture 53 to be about 90% of the widest outside diameter of the pipette tip, allowing the seal to compress around the tip while relaxing to its normal shape when removed from the aspiration hole. Conversely, the rigid collar 51 has an aperture that is oversized 10% with respect to the outside diameter of the pipette tip 34 allowing it to easily receive the pipette tip. The collar's aperture is decreased when the set screw 52 is tightened to secure the collar about the pipette tip 34. In an alternative embodiment, the seal 35 could also be integrally molded with the pipette tip 34. In yet another embodiment, a soft sealing material could be used around the upper edge 24 of the aspiration holes so as to sealingly receive a tip without the seal 35.

The MWP 10 is used to promote tissue growth and propagation by supplying nutrients in a sterile environment. The method for using the MWP includes loading the plate either manually, or using a cell-sorter modified to sort tissue samples, such as those used to sort fruit flies. Generally, this equipment uses a vacuum to pick up the samples. The unmodified cell sorter could be used if the tissue samples are small enough. The MWP 10 is preferably covered with a transparent, polystyrene cover or lid to allow the transmission of light to the tissue.

Once the tissue 32 is in the wells 16 of the plate, the plate is stacked for access by a liquid handler including multiple pipette tips connected to media and vacuum supplies. The liquid handler grips the plate and removes the lid in a manner known to those of skill in the art. The liquid handling device extends each pipette tip 34 into a respective one of the aspiration holes 22 until the seal 35 abuts the upper edge 24 of the aspiration hole and the portion of the upper surface 14 thereabout. The liquid handling device dispenses media through the tips, into the aspiration holes 22, through the channels 28 and into the wells 16. In this manner, the tissue 32 in each of the wells 16 has access to a supply of the media through the frit 30. The lid is replaced on the plate 10 and the plate is placed in a culture room with illumination to promote growth (in the case of plant tissues).

After the tissue depletes essential nutrients in the media 36, or the media otherwise needs to be changed, the plate 10 is loaded back on the liquid handling device. The lid is removed from the plate. The liquid handling device extends each pipette tip 34 into a respective one of the aspiration holes 22 until the seal 35 abuts the upper edge 24 of the aspiration hole and the portion of the upper surface 14 thereabout. The liquid handling device applies a vacuum or suction pressure through the pipette tips which draws the media from the cell wells 16, through the channels 28, into the aspiration holes 22 and into the pipette tips to complete aspiration. The media is cycled as often as needed by repeating the above process.

Figure 4:
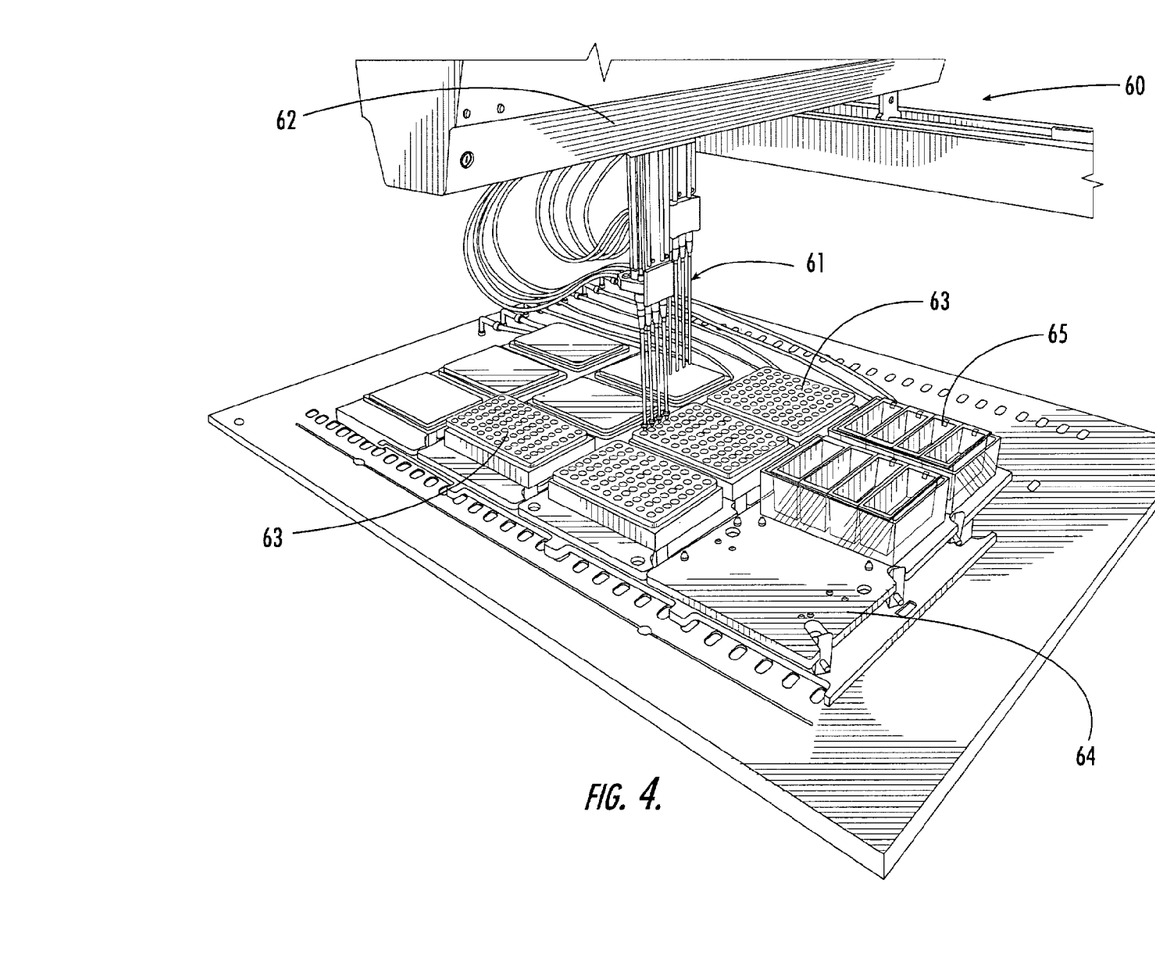
FIG. 4 is a perspective view of a system for replenishing media in the MWP shown in FIG. 1 of another embodiment of the present invention.

In another embodiment, an automated pipetting head (or robotic liquid handler) 60 is used to address single or multiple wells selectively, such as the GENESIS liquid handler (TECAN, AG of Switzerland), shown in FIG. 4. The robot is upgraded with a six-way valve for switching between different media, reagent and ethanol supplies. The robot includes eight pipetting tips 61 on its liquid handling arm 62. Four of the tips are configured to deliver media to a plurality of multiple well plates 63 supported on its deck 64. The four remaining tips are each fitted with a tip seal allowing the four remaining tips to aspirate the wells 16 through their respective aspiration holes 22.

Preferably, the robotic liquid handler 60 is operated using a software program to control deployment of its pipetting tips 61 in such a way as to minimize cross-contamination between the wells 16. During media delivery, contamination of the four media supplying tips is avoided by suspending the media supplying tips over the wells without contacting the plates. Contamination of the aspiration tips is avoided by flushing each tip with an anti-microbial ethanol liquid in between aspiration cycles. The exterior of the tips and seals are washed in an on-deck shallow wash station 65, also filled with ethanol liquid. The ethanol is pumped by a syringe pump and/or a high-speed diaphragm (fast wash) pump from a reservoir accessible through the six way valve.

Programming the robot 60 to access the correct holes requires teaching the robot the location of both the aspiration holes 22 and the wells 16. In this manner, the robot is operated as if the plate 10 has twice as many wells because the aspiration holes 22 are positioned to correspond to the wells of a plate having twice the density. The fact that the aspiration holes have a smaller diameter than the wells 16 is of no consequence as the robot seeks the center of the aspiration holes 22. For instance, the robot is programmed to access a 24 well plate as if it had 48 wells, each well having a diameter equal to that of the aspiration holes. Notably, the programming of the well centers (or their locations with respect to the aspiration holes) can be considerably off because of the much smaller diameter of the pipette tips 61 with respect to the wells.

Figure 5:
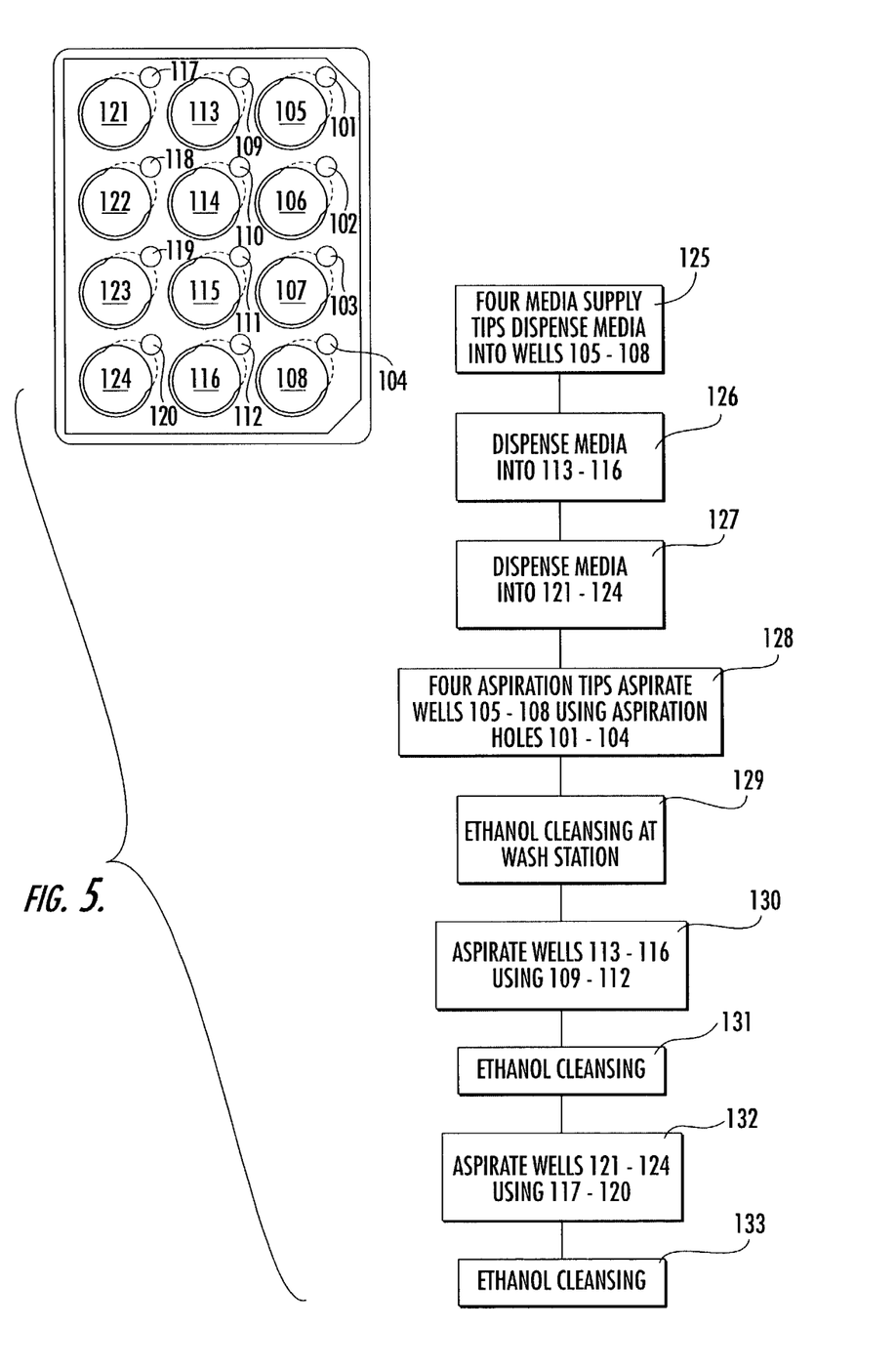
FIG. 5 is a flow chart of a method of replenishing media using the system of FIG. 4.

FIG. 5 depicts one example of how the robot 60 can be programmed to address the wells 16 and aspiration holes 22 of the plate 10. First, the four media supply tips are positioned above wells 105 through 108 and, without contacting the plate 10, dispense media into the wells in step 125. The media supply tips are then sequentially positioned above, and dispense media into, wells 113 through 116 and 121 through 124 in steps 126 and 127, respectively. The four aspiration tips are then inserted into the aspiration holes (which the robot recognizes as "wells") 101 through 104, aspirating spent media from wells 105 through 108, in step 128. After aspiration, the aspiration tips are flushed internally and cleansed externally with ethanol at the wash station 65, in step 129. Aspiration and cleaning are alternated for holes 109 through 112, in steps 130 and 131, and again for aspiration holes 117 through 120 in steps 132 and 133. It should be noted that the process can be expanded or reduced depending upon the number of pipetting tips and the number of wells. In addition, the process is preferably performed within a HEPA filtered environment, such as within a pressurized and filtered hood, to minimize the occurrence of contamination.

The robot 60 can also be used in conjunction with a high-density hotel or rack for holding and supplying light to the tissue in hundreds of the plates, as described in commonly owned U.S. patent application Ser. No. 10/080,918 entitled, "LED Array for Illuminating Cell Well Plates and Automated Rack System for Handling the Same," which is incorporated herein by reference. The automated rack system uses its own robot to manipulate and present the plates to the robot of the present system.

In yet another embodiment, the well plate and method of the present invention could be used to perform solid phase extraction. Each well of the well plate contains a matrix trapped between a pair of frits which form a column. Various compounds (such as a ligands, or antibodies) are forced through the column and become trapped within the matrix. After solid phase extraction, an agent can be forced through the column to breakup the solid phase. High-throughput distribution and retrieval of the compound, agents, etc. could be handled by an automated pipetting head using the wells and their respective aspiration holes.

The present invention has several advantages. For example, the tissue samples 32 in the wells 16 do not have to be moved or disturbed, cutting down on workload, ensuring sterile and optimal growth conditions. The plates 10 may be used with conventional liquid handling pipette heads because the aspiration holes 22 are accessible from the upper surface of the body, i.e., a top-loading arrangement. The use of robotic liquid handlers with the plate promotes a well-to-well consistency in the treatment of the tissue, as well as the efficient removal and replacement of the media 36. The top-loading aspect allows the use of a standard lid for sterility control and removes the need for a separate vacuum manifold station for pulling out media. The lack of a manifold allows for the differential treatment of each well and provides flexibility in liquid handler design and selection. The liquid head can be configured to remove the media as well as add new media with no change of tooling or pipette tips.

Some of the figures disclosed herein contain block diagrams, flowcharts and control flow illustrations of methods, systems and program products according to the invention. It will be understood that each block or step of the block diagram, flowchart and control flow illustration, and combinations of blocks in the block diagram, flowchart and control flow illustration, can be implemented by computer program instructions. These computer program instructions may be loaded onto a computer or other programmable apparatus to produce a machine, such that the instructions which execute on the computer or other programmable apparatus create means for implementing the functions specified in the block diagram, flowchart or control flow block(s) or step(s). These computer program instructions may also be stored in a computer-readable memory that can direct a computer or other programmable apparatus to function in a particular manner, such that the instructions stored in the computer-readable memory produce an article of manufacture including instruction means which implement the function specified in the block diagram, flowchart or control flow block(s) or step(s). The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions specified in the block diagram, flowchart or control flow block(s) or step(s).

Accordingly, blocks or steps of the block diagram, flowchart or control flow illustration support combinations of means for performing the specified functions, combinations of steps for performing the specified functions and program instruction means for performing the specified functions. It will also be understood that each block or step of the block diagram, flowchart or control flow illustration, and combinations of blocks or steps in the block diagram, flowchart or control flow illustration, can be implemented by special purpose hardware-based computer systems which perform the specified functions or steps, or combinations of special purpose hardware and computer instructions.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. For instance, in another embodiment the well plate and method could also be used to grow bacterium. Although specific terms are employed herein, they are used in a generic and descriptive sense only and not for purposes of limitation.

That which is claimed:

1. An assembly for supporting a tissue which is to be bathed in a media that is regularly aspirated and refreshed by a top-loading pipette device, said assembly comprising:
    a porous frit; and
    a body having an upper surface, said body defining:
        a first hole having a first hole upper edge defined by the upper surface of the body and a first hole bottom portion defined within the body and below the upper surface of the body, said first hole being configured to receive the porous frit and the tissue and to hold the media bathing the porous frit and the tissue;
        a crescent-shaped ledge protruding into the first hole bottom portion and configured to support the frit thereon; and
        a second hole having a second hole upper edge defined by the upper surface of the body and a second hole bottom portion defined within the body and below the upper surface of the body, the second hole bottom portion being connected in fluid communication with the first hole bottom portion such that the pipette device can access the first hole through the second hole upper edge to aspirate the media through vacuum application and refresh the media by pumping in fresh media without removal of the tissue and the porous frit from the plate.

2. An assembly of claim 1, wherein the top surface of the body is configured to receive a cover plate disposed thereon.

3. An assembly of claim 2, further comprising a cover plate that is transparent to light transmission and wherein the first hole upper edge is configured to allow light transmission to the tissue contained in the first hole by having a height to diameter ratio of less than 2 to 1 so that growth of the tissue is promoted.

4. An assembly of claim 1, wherein the second hole has a diameter that is compatible with pre-existing pipette tips.

5. An assembly of claim 1, wherein the body is formed from a single piece of material.

6. An assembly for supporting a tissue which is to be bathed in a media that is regularly aspirated and refreshed by a top-loading pipette device, said assembly comprising:
    a porous frit;
    a body being formed from a single piece of material and having an upper surface, said body defining:
        a first hole having a first hole upper edge defined by the upper surface of the body and a first hole bottom portion defined within the body and below the upper surface of the body, said first hole being configured to receive the porous frit and the tissue and to hold the media bathing the porous frit and the tissue; and
        a second hole having a second hole upper edge defined by the upper surface of the body and a second hole bottom portion defined within the body and below the upper surface of the body, the second hole bottom portion being connected in fluid communication with the first hole bottom portion such that the pipette device can access the first hole through the second hole upper edge to aspirate the media through vacuum application and refresh the media by pumping in fresh media without removal of the tissue and the porous frit from the plate.

7. An assembly of claim 6, wherein the porous frit is constructed of a sintered polyethylene material.

8. An assembly of claim 7, wherein the frit is hydrophilic.

9. An assembly of claim 6, wherein the frit is about 0.25 inches thick.

10. An assembly of claim 6, wherein the frit has a pore size of 90 to 130 micrometers.

11. An assembly of claim 6, wherein the body further comprises a ledge protruding into the first hole bottom portion and configured to support the frit thereon.

12. An assembly of claim 1, wherein the porous frit is constructed of a sintered polyethylene material.

13. An assembly of claim 12, wherein the frit is hydrophilic.

14. An assembly of claim 1, wherein the frit is about 0.25 inches thick.

15. An assembly of claim 1, wherein the frit has a pore size of 90 to 130 micrometers.

* * * * *